United States Patent [19]

Scholl et al.

[11] 4,177,206

[45] Dec. 4, 1979

[54] POLYISOCYANATES CONTAINING SULPHONIC ACID AND PHOSPHONATE GROUPS

[75] Inventors: Hans-Joachim Scholl, Cologne; Dieter Dieterich, Leverkusen, both of Fed. Rep. of Germany

[73] Assignee: Bayer Aktiengesellschaft, Leverkusen, Fed. Rep. of Germany

[21] Appl. No.: 907,515

[22] Filed: May 19, 1978

[30] Foreign Application Priority Data

Jun. 3, 1977 [DE] Fed. Rep. of Germany ....... 2725208

[51] Int. Cl.$^2$ ................ C07C 119/048; C07C 143/24; C07C 143/68; C07F 9/09
[52] U.S. Cl. .......................... 260/456 P; 260/453 AR; 260/453 AM; 260/453 AB; 260/939; 260/969; 560/26; 528/72
[58] Field of Search ............. 260/453 AR, 939, 556 P

[56] References Cited

U.S. PATENT DOCUMENTS

| | | | |
|---|---|---|---|
| 3,240,726 | 3/1966 | Oertel et al. | 260/939 |
| 3,959,329 | 5/1976 | Dieterich et al. | 260/453 AR |

*Primary Examiner*—Dolph H. Torrence
*Attorney, Agent, or Firm*—Gene Harsh; Joseph C. Gil; R. Brent Olson

[57] ABSTRACT

The present invention is directed to polyisocyanate mixtures which are liquid at room temperature and which (a) contain from 10 to 42% by weight of aromatically-bound isocyanate groups, which may be partly in the form of carbamic acid chloride;

(b) contain from 0.5 to 5% by weight of sulphur in the form of sulphonic acid groups which may be at least partly neutralized or esterified;

(c) contain from 0.5 to 5% by weight of phosphorus in the form of phosphonic acid alkyl ester groups or phosphonic acid aralkyl ester groups and (d) have a viscosity of from 10 to 50,000 cP at 25° C.

7 Claims, No Drawings

POLYISOCYANATES CONTAINING SULPHONIC ACID AND PHOSPHONATE GROUPS

BACKGROUND OF THE INVENTION

Polyisocyanates containing sulphonic acid groups are already known and are described, e.g., in German Offenlegungsschriften Nos. 2,227,111; 2,359,614; 2,359,615; 2,524,476 and 1,939,911. In their preparation, liquid multi-component mixtures of aromatic polyisocyanates are mixed with sulphur trioxide or an equivalent quantity of oleum, sulphuric acid or chlorosulphonic acid and left to react.

Polyisocyanates containing phosphonate groups are also already known and are described, e.g., in German Offenlegungsschrift No. 1,127,583. These phosphorus-containing isocyanates may be prepared, for example, by converting polyisocyanates into carbamic acid halides by the action of hydrogen chloride and then reacting these carbamic acid halides with equivalent quantities, based on the carbamic acid halide groups, of trialkyl phosphites by an Arbusow-type reaction.

Polyisocyanates which contain both sulphonic acid groups and phosphonate groups, however, have not hitherto been known. It is therefore necessary, for example, when producing inorganic-organic synthetic resins as described in German Offenlegungsschrift No. 2,227,147 to increase the flame-resistance of these synthetic resins by adding unreactive low molecular weight phosphoric acid esters such as trichloroethyl phosphate during the manufacturing process. This method has, however, serious disadvantages in that, if the desired mechanical properties are to be obtained, only limited quantities of these low molecular weight compounds, insufficient for providing complete flame-resistance, may be added. Moreover, the low molecular weight compounds added tend to migrate from the synthetic resin due to their low molecular weight.

It was therefore an object of the present invention to provide new polyisocyanates containing both sulphonic acid groups and chemically fixed phosphorus. This problem could be solved by the process according to the invention, which is described below.

DESCRIPTION OF THE INVENTION

The present invention is directed to polyisocyanate mixtures which are liquid at room temperature and which (a) contain from 10 to 42% by weight of aromatically-bound isocyanate groups, which may be partly in the form of carbamic acid chloride;

(b) contain from 0.5 to 5% by weight of sulphur in the form of sulphonic acid groups which may be at least partly neutralized or esterified;

(c) contain from 0.5 to 5% by weight of phosphorus in the form of phosphonic acid alkyl ester groups or phosphonic acid aralkyl ester groups and (d) have a viscosity of from 10 to 50,000 cP at 25° C.

The invention also relates to a process for the preparation of such polyisocyanate mixtures, which is characterized in that aromatic polyisocyanates or polyisocyanate mixtures are reacted with chlorosulphonic acid at a temperature of from −10° C. to 150° C. in the presence of a trialkyl or triaralkyl phosphite which may be substituted with halogen.

Suitable starting materials for the process according to the invention include any organic compounds which have at least two aromatically-bound isocyanate groups, are unsubstituted in at least one ortho- or para-position to an aromatically-bound isocyanate group and, apart from the isocyanate groups and the aromatic rings which are capable of being substituted, are inert under the reaction conditions and, lastly, have a melting point or softening point below 70° C., as well as mixtures of such polyisocyanates having a melting or softening point below 40° C., in which mixtures some of the components may also have a melting or softening point above 70° C. The following are examples of suitable aromatic polyisocyanates: 3,3'- and 2,2'-dimethyl-4,4'-diisocyanato-diphenyl methane; 2,5,2',5'-tetramethyl-4,4'-diisocyanato-diphenyl methane; 3,3'-dimethoxy-4,4'-diisocyanato-diphenyl methane; 3,3'-dichloro-4,4'-diisocyanato-diphenyl methane; 4,4'-diisocyanato-diphenyl sulphone; 4,4'-diisocyanato-diphenyl ether; 4,4'-diisocyanato-3,3'-dibromo-diphenyl methane; 4,4'-diisocyanato-3,3'-diethyl-diphenyl methane; 4,4'-diisocyanato-diphenyl sulphide; 1,3- and 1,4-phenylene diisocyanate; 2,4- and 2,6-tolylene diisocyanate and any mixtures of these isomers; diphenyl methane-2,4'- and/or -4,4'-diisocyanate; naphthylene-1,5-diisocyanate; triphenyl methane-4,4',4"-triisocyanate; polyphenyl-polymethylene polyisocyanates which can be obtained by aniline-formaldehyde condensation followed by phosgenation and which have been described in, for example, British Pat. No. 874,430 and 848,671; polyisocyanates with carbodiamide groups as described in German Pat. No. 1,092,007; diisocyanates of the kind described in U.S. Pat. No. 3,492,330; polyisocyanates with allophanate groups as described in, for example, British Pat. No. 994,890, Belgian Pat. No. 761,626 and published Dutch patent application No. 7,102,524; polyisocyanates with isocyanate groups as described in, for example, German Pat. Nos. 1,022,789; 1,222,067 and 1,027,394 and in German Offenlegungsschriften Nos. 1,929,034 and 2,004,048; polyisocyanates with acrylated urea groups as described in German Pat. No. 1,230,778; and polyisocyanates with biuret groups as described in, for example, German Pat. No. 1,101,394, British Pat. No. 889,050 and French Pat. No. 7,017,514. The distillation residues obtained from the commercial production of isocyanates and still containing isocyanate groups may also be used, optionally dissolved in one or more of the above mentioned polyisocyanates. Any mixtures of the above mentioned polyisocyanates may also be used, provided that they fulfil the conditions mentioned above regarding the melting or softening point.

Phosgenation products of condensates of aniline and aldehydes or ketones, e.g. of acetaldehyde, propionaldehyde, butyraldehyde, acetone or methyl-ethyl ketone, are also suitable. The phosgenation products of condensates of anilines which are alkyl substituted on the nucleus, particularly of toluidenes with aldehydes or ketones such as formaldehyde, acetaldehyde, butyraldehyde, acetone or methyl-ethyl ketone may also be used.

Also suitable are the reaction products of the above mentioned aromatic polyisocyanate mixtures with from 0.2 to 50 equivalents % of polyols, provided that the viscosity of the resulting reaction products does not exceed 30,000 cP at 25° C. and the isocyanates content of the reaction products is at least 15% by weight. Suitable polyols for modifying the starting materials are, in particular, the polyether and/or polyester polyols known from polyurethane chemistry which have molecular weights in the range of from 200 to 6000, preferably from 300 to 4000, as well as low molecular weight polyols with molecular weights from 62 to 200. Examples of such low molecular weight polyols include ethylene glycol, propylene glycol, glycerol, trimethylol propane and 1,4,6-hexane triol.

Aromatic polyisocyanates suitable for the process according to the invention generally have an isocyanate content of from 15 to 53% by weight, preferably 25 to 48% by weight and most preferably 25 to 35% by weight.

Liquid multi-component mixtures of aromatic polyisocyanates having an isocyanate content of from 20 to 48% by weight and preferably 25 to 35% by weight, and an average isocyanate functionality of 2.0 are particularly suitable for the process according to the invention.

Preferred liquid aromatic polyisocyanate mixtures for the process according to the invention are the phosgenation products of aniline-formaldehyde condensates which contain from 20 to 90% by weight of dinuclear diisocyanates, from 3 to 40% by weight of trinuclear triisocyanates, from 1 to 20% by weight of tetranuclear tetraisocyanates and from 1 to 40% by weight of higher nuclear polyisocyanates.

Commercial tolylene diisocyanate mixtures are also suitable for the process according to the invention. Commercial distillation residues of the kind which are obtained from the distillation of commercial tolylene diisocyanate mixtures and which contain less than 70% by weight of free tolylene diisocyanate isomers are also eminently suitable. Such distillation residues can be obtained, for example, by the process described in German Offenlegungsschrift No. 2,035,731. The distillation residues described in German Offenlegungsschrift No. 2,123,183 and their solutions in phosgenation products of anilineformaldehyde condensates, are also particularly suitable.

In addition to the aromatic polyisocyanates of which examples have been given above and chlorosulphonic acid, trialkyl phosphites or tris-(aralkyl)-phosphites, with or without halogen substitutents, are used for the process according to the invention, i.e. compounds represented by the formula

P(OR)$_3$, in which
R represents an aliphatic hydrocarbon group with from 1 to 18, preferably 1 to 4 carbon atoms which may be substituted with halogen, preferably with chlorine, or an araliphatic hydrocarbon group with a total of 7 to 15 carbon atoms, preferably 7 or 8 carbon atoms, which may be substituted with halogen, and preferably chlorine.

Phosphites represented by the above formula which have different R groups are, of course, also suitable for the process according to the invention. Examples of suitable phosphites include trimethyl phosphite, triethyl phosphite, tris-(2-chloroethyl)-phosphite, tributyl phosphite, trioctyl phosphite, tribenzyl phosphite and O,O'-dimethyl-O''-(2-chloroethyl)-phosphite. The trialkyl phosphites mentioned as examples are preferred. Tris-(halogen alkyl)-phosphites are particularly preferred, in particular tris-(2-chloroethyl)-phosphite.

In the process according to the invention, the reactants are preferably used in such quantities that from 0.01 to 0.5, preferably from 0.02 to 0.3 and most preferably from 0.03 to 0.2 mol of chlorosulphonic acid and from 0.01 to 0.5, preferably from 0.02 to 0.3 and most preferably from 0.03 to 0.2 mol of phosphite enter into the reaction per mol of aromatically-bound isocyanate groups. The phosphite and chlorosulphonic acid are generally used in equimolar quantities although they may also be used in different molar quantities.

The process according to the invention is carried out within a temperature range of from −10° C. to 150° C., preferably from 0° to 100° C.

The reaction according to the invention may either be carried out by mixing all three of the reactants together or it may be carried out as a two-stage process in which the polyisocyanate is first reacted with chlorosulphonic acid and this reaction is followed by the reaction with the phosphite. The process according to the invention may be carried out either in the presence of solvents which are inert towards the starting materials and the end products of the process under the reaction conditions or, particularly when using low viscosity starting materials, it may be carried out under solvent-free conditions. The solvents used are preferably halogenated hydrocarbons such as dichloroethane, trichloroethane, fluorotrichloro methane, methylene chloride or chlorobenzene. They preferably have a boiling point of from 0° C. to 140° C. The reaction according to the invention may also be carried out under pressure if desired. If inert solvents are used, the concentration of the reactants in the solvent may vary within wide limits but the solvents are generally used in such quantities that the reactants are at a concentration of from 20 to 100% by weight in the solution during the reaction according to the invention, this concentration indicating the percent by weight of all the reactants, based on the weight of the whole solution.

To carry out the process according to the invention, the polyisocyanate is preferably mixed with the phosphite and any solvent used, and the chlorosulphonic acid, which may also be dissolved in an inert solvent, is added to this mixture within a period of from several minutes to several hours with stirring. The chlorosulphonic acid is preferably added at room temperature and the reaction mixture is then heated to 50° to 100° C. to complete the reaction.

The chemical reactions which take place in the process according to the invention are illustrated by the example of the reaction between an aromatic diisocyanate R'(NCO)$_2$ (R' represents the aromatic hydrocarbon group of an aromatic diisocyanate), chlorosulphonic acid and a phosphite P(OR)$_3$ (R has the meaning already indicated):

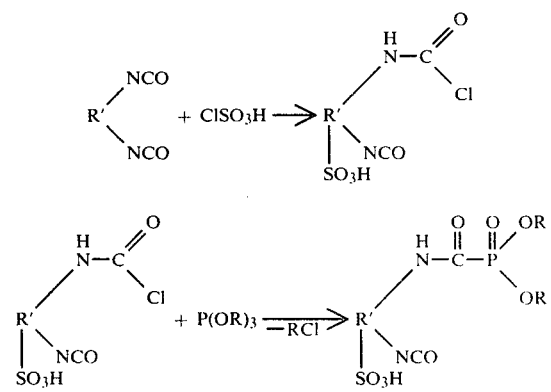

It is presumed that chlorosulphonic acid reacts to form sulphonated carbamic acid chlorides which then undergo an Arbusow reaction to form the products according to the invention. It is surprisingly found that the reactions proceed uniformly under the given conditions although side-reactions would be expected from the combination of phosphite/chlorosulphonic acid (e.g. Houben Weyl, Fourth Edition, Volume XII/2, 1964 page 79 et seq.)

It is particularly surprising that the products obtained by the process according to the invention are liquid even when tolylene diisocyanate and phosgenation products of aniline-formaldehyde condensates containing a high proportion of 4,4'-dinuclear products are used, and in particular when not more than 0.2 mol of chlorosulphonic acid and not more than 0.2 mol of organic phosphite are used to one isocyanate equivalent.

The liquid polyisocyanates with sulphonic acid and phosphate groups obtained by the process according to the invention are characterized by
(a) an isocyanate content of from 10 to 42% by weight, preferably from 25 to 35% by weight,
(b) a sulphur content of from 0.5 to 5% by weight,
(c) a phosphorus content of from 0.5 to 5% by weight, and
(d) a viscosity of from 10 to 50,000 cP, preferably from 100 to 20,000 cP, at 25° C.

When chlorosulphonic acid is used in a molar excess based on the quantity of phosphite, the isocyanate groups are partly in the form of carbamic acid chloride groups in the products obtained by the process according to the invention. The numerical values given for the isocyanate content of the products according to the invention include any isocyanate groups present in the form of carbamic acid chloride groups, and, in such cases, the isocyanate content is also calculated on the basis of the molecular weight of the isocyanate group (42). Since, as will be explained more fully below, the sulphonic acid groups can easily be at least partly neutralized or esterified after the reaction according to the invention, the sulphur content given refers to all the sulphonic acid groups present, which may be in an at least partly neutralized or esterified form in the products of the process.

The aromatic polyisocyanates with sulphonic acid and phosphate groups according to the invention are valuable starting materials for the production of molded products and non-cellular synthetic resins. They can easily be processed by the usual methods such as casting and by means of the usual conveyer and dosing systems. After their preparation, the aromatic phosphonated isocyanatosulphonic acids obtained by the process according to the invention may be partly or completely converted into the corresponding isocyanatosulphonates by a neutralization reaction.

The neutralization agents used may be organic or inorganic bases such as trimethylamine, triethylamine, tributylamine, dimethyl aniline, urotropine, sodium bicarbonate, sodium hydroxide, calcium carbonate, magnesium carbonate, calcium hydroxide, magnesium hydroxide, magnesium oxide, zinc oxide or sodium phosphate. Inorganic neutralizing agents which are not strongly basic in their reactions, such as calcium carbonate, magnesium carbonate, dolomite, chalk or sodium phosphate may be used in large excess as fillers. The hydrophilic character and reactivity of the products according to the invention are increased by the conversion of the sulphonic acid groups into the corresponding sulphonate groups. Conversion of the corresponding phosphonated isocyanato sulphonic acids into sulphonic acid esters with epoxides or oxatones can also be used successfully for reducing the proportion of acid. Epoxides suitable for this purpose include ethylene oxide, propylene oxide and epichlorohydrin.

Starting materials for the examples described below:

$A_1$—The crude phosgenation product of an aniline/formaldehyde condensate is distilled to remove diisocyanatodiphenyl methane until the distillation residue has a viscosity of 100 cP at 25° C. (dinuclear content: 59.7% by weight, trinuclear content: 21.3% by weight, higher nuclear polyisocyanate content: 19.0% by weight). Isocyanate content: 31.5% by weight.

$A_2$—A similarly prepared polyisocyanate having a viscosity of 200 cP at 25° C. (dinuclear content: 44.3% by weight, trinuclear content: 23.5% by weight; higher nuclear polyisocyanate content: 32.2% by weight). Isocyanate content: 31.1% by weight.

$A_3$—A similarly prepared polyisocyanate having a viscosity of 400 cP at 25° C. (dinuclear content: 45.1% by weight; trinuclear content: 22.3% by weight; higher nuclear polyisocyanate content: 32.6%). Isocyanate content: 30.9% by weight.

$A_4$—Mixture of tolylene-2,4-diisocyanate and tolylene-2,6-diisocyanate in proportions of 80:20. Isocyanate content: 48% by weight.

$A_5$—40% solution in $A_4$ of a distillation residue obtained from the distillation of $A_4$. Isocyanate content: 38.3% by weight.

$A_6$—Prepolymer of 90% by weight of $A_2$ and 10% by weight of a polyethylene gylcol with hydroxyl number 250 and viscosity 21,000 cP at 25° C. which has been started on trimethylol propane. Isocyanate content: 26.2% by weight.

EXAMPLES

EXAMPLE 1

1000 g of polyisocyanate $A_3$ and 78.5 g of tris-(2-chloroethyl)-phosphite are introduced into the reaction vessel. 41.3 g of chlorosulphonic acid in 17 g of methylene chloride are added dropwise at 20° to 30° C. over a period of 2 hours. The reaction mixture is then stirred for 1 hour at 100° C. A product having the following properties is obtained:

Sulphur content: 1.0%
Phosphorus content: 0.8%
Isocyanate content: 26.5%
Viscosity (25° C.): 1200 cP Similarly prepared products are indicated in Table 1. In some of the examples, dichloroethane was used as solvent and distilled off at 50° C./20 Torr after the reaction.

TABLE 1

| Example | Isocyanate | $CH_2ClCH_2Cl$ | $CH_2Cl_2$ | $ClSO_3H$ | $P(OC_2H_4Cl)_3$ | Temp. °C. | After-stirring | S % by weight | P % by weight | NCO % by weight | Viscosity cP/25° C. |
|---|---|---|---|---|---|---|---|---|---|---|---|
| 1 | 1000 g $A_3$ | — | 17g | 41.3g | 78.5g | 20–30 | 1 hr. | | | | |

TABLE 1-continued

| Example | Isocyanate | CH$_2$ClCH$_2$Cl | CH$_2$Cl$_2$ | ClSO$_3$H | P(OC$_2$H$_4$Cl)$_3$ | Temp. °C. | After-stirring | S % by weight | P % by weight | NCO % by weight | Viscosity cP/25° C. |
|---|---|---|---|---|---|---|---|---|---|---|---|
| | | | | | | | 100° C. | 1.0 | 0.8 | 26.5 | 1200 |
| 2 | 1000 g A$_3$ | — | 16g | 40.1g | 48.0g | 20–30 | " | 1.0 | 0.5 | 27.0 | 2000 |
| 3 | 1000 g A$_3$ | — | 10g | 24.5g | 47.0g | 20–30 | 1 hr. 80° C. | 0.5 | 0.5 | 29.0 | 650 |
| 4 | 1000 g A$_3$ | — | 24g | 58.8g | 111.8g | 20–30 | 1 hr. 50° C. | 1.4 | 1.1 | 25.0 | 1100 |
| 5 | 1000 g A$_3$ | — | 24g | 58.8g | 111.8g | 20–30 | 1 hr. 80° C. | 1.4 | 1.1 | 25.5 | 1800 |
| 6 | 1000 g A$_3$ | — | 24g | 58.8g | 111.8g | 20–30 | 1 hr. 100° C. | 1.4 | 1.1 | 25.3 | 2300 |
| 7 | 1000 g A$_3$ | — | 74g | 178.0g | 385.0g | 20–30 | 1 hr. 80° C. | 3.0 | 2.7 | 16.8 | 8000 |
| 8 | 1000 g A$_3$ | — | 118g | 294.0g | 617.0g | 20–30 | " | 4.0 | 3.5 | 12.0 | 45000 |
| 9 | 1000 g A$_3$ | 411g | — | 58.8g | 111.8g | 20–30 | 1.5 hr. 50° C., 20 mm | 1.4 | 1.1 | 25.6 | 2100 |
| 10 | 1000 g A$_2$ | — | 17g | 41.3g | 78.5g | 20–30 | 1 hr. 80° C. | 1.0 | 0.8 | 26.4 | 1000 |
| 11 | 1000 g A$_1$ | — | 24g | 58.8 | 111.8g | 20–30 | " | 1.4 | 1.1 | 25.2 | 900 |
| 12 | 1000 g A$_4$ | — | 24g | 58.8 | 111.8g | 20–30 | 1 hr. 100° C. | 1.4 | 1.1 | 38.8 | 300 |
| 13 | 1000 g A$_4$ | — | 57g | 143.5 | 171.0g | 20–30 | 1.5 hr. 100° C. | 3.0 | 1.5 | 32.0 | 300 |
| 14 | 1000 g A$_4$ | 411g | — | 58.8 | 111.8g | 20–30 | 1.5 hr. 50° C., 20 mm | 1.4 | 1.1 | 37.9 | 300 |
| 15 | 1000 g A$_5$ | — | 24g | 58.8 | 111.8g | 20–30 | 1 hr. 80° C. | 1.4 | 1.1 | 30.3 | 4700 |
| 16 | 1000 g A$_6$ | — | 24g | 58.8 | 111.8g | 20–30 | " | 1.4 | 1.1 | 20.4 | 7000 |

What is claimed is:

1. Polyisocyanate mixtures which are liquid at room temperature and which
    (a) contain from 10–42%, by weight of aromatically bound isocyanate groups optionally partly present in the form of carbamic acid chloride,
    (b) contain from 0.5–5% by weight of sulphur in the form of sulphonic acid groups which may be partly neutralized or esterified,
    (c) contain from 0.5–5% by weight of phosphorus in the form of phosphonic acid alkyl ester groups or phosphonic acid aralkyl ester groups and
    (d) have a viscosity of from 10–50,000 cP at 25° C., and which are prepared by reacting aromatic polyisocyanate mixtures with chlorosulphonic acid at −10° C. in the presence of a trialkyl phosphite or tris-(aralkyl)-phosphite which may be substituted with halogen.

2. The mixtures of claim 1 which have an isocyanate content of from 25 to 35% by weight, and a viscosity of from 100 to 20,000 cP at 25° C.

3. A process for the preparation of liquid polyisocyanate mixtures comprising reacting aromatic polyisocyanates or polyisocyanate mixtures with chlorosulphonic acid at −10° C. to 150° C. in the presence of a trialkyl phosphite or tris-(aralkyl)-phosphite which may be substituted with halogen.

4. The process according to claim 3, characterized in that the reaction is carried out in the presence of solvents which are inert under the reaction conditions.

5. The process according to claim 3, characterized in that the trialkyl phosphite used is tris-(2-chloroethyl)-phosphite.

6. The process of claim 3 wherein from 0.01 to 0.5 mols of chlorosulphonic acid and from 0.01 to 0.5 mols of phosphite per mol of aromatically-bound isocyanate groups are used.

7. The process of claim 3 wherein the reaction temperature is from 0° to 100° C.

* * * * *